(12) United States Patent
Lin et al.

(10) Patent No.: US 9,289,008 B1
(45) Date of Patent: Mar. 22, 2016

(54) HIGH TEMPERATURE, RESISTANT PROBIOTICS FOR FOOD AND FEED PREPARATIONS

(71) Applicants: Jhy-Jhu Lin, Potomac, MD (US); Susheel Bhanu Busi, Frederick, MD (US)

(72) Inventors: Jhy-Jhu Lin, Potomac, MD (US); Susheel Bhanu Busi, Frederick, MD (US)

(73) Assignee: Imaglin Technology, LLC, Frederick, MD (US)

( * ) Notice: Subject to any disclaimer, the term of this patent is extended or adjusted under 35 U.S.C. 154(b) by 32 days.

(21) Appl. No.: 13/676,579

(22) Filed: Nov. 14, 2012

Related U.S. Application Data (60) Provisional application No. 61/629,083, filed on Nov. 14, 2011.

(51) Int. Cl.
  *C12N 1/20* (2006.01)
  *A23L 1/30* (2006.01)
  *C12R 1/01* (2006.01)
(52) U.S. Cl.
  CPC ............... *A23L 1/3014* (2013.01); *C12R 1/01* (2013.01); *A23V 2002/00* (2013.01)

(58) Field of Classification Search
  None
  See application file for complete search history.

(56) References Cited

U.S. PATENT DOCUMENTS 6,692,779 B2 * 2/2004 Dominques et al. ............ 426/61
7,579,030 B2 * 8/2009 Domingues et al. ............ 426/61

OTHER PUBLICATIONS

Perez Guerra et al. "Production of four potentially probiotic lactic acid bacteria and their evaluation as feed additives for piglets". Animal Feed Science and Technology. Mar. 1, 2007, vol. 134, No. 1-2, pp. 89-107.*
Lin et al. "Probiotics as alternative biomedicines for pets with digestive disorders". Proceedings of 8th Annual Meeting of JBVP, Sep. 2006, pp. 288-293.*
Mandal et al. "Optimized culture conditions for bacteriocin production by *Pediococcus acidilactici* LAB 5 and its characterization". Indian Journal of Biochemistry and Biophysics. Apr. 2008, vol. 45, pp. 106-110.*

* cited by examiner

*Primary Examiner* — Vera Afremova
(74) *Attorney, Agent, or Firm* — Stein IP, LLC (57) ABSTRACT

A *Pediococcus acidilactici* strain that is viable at temperatures above 65° C., is able to grow in aerobic and anaerobic conditions, and in a pH range between 1 and 6.2 and a consumable food product containing same.

10 Claims, 2 Drawing Sheets

Figure 1

Total number of *Pediococcus acidilactici* colonies after pH tolerance selection at pH 5.0, 5.5 and 6.2 (control) is >4.8 x 10⁵

Figure 2

HIGH TEMPERATURE, RESISTANT PROBIOTICS FOR FOOD AND FEED PREPARATIONS

CROSS-REFERENCE TO RELATED APPLICATIONS

This application claims the benefit of U.S. Provisional Application No. 61/629,083, filed Nov. 14, 2011 in the U.S. Patent and Trademark Office, the disclosures of which are incorporated herein by reference.

BACKGROUND OF THE INVENTION

1. Field of the Invention

Probiotics are beneficial microorganisms naturally existing in the gastrointestinal (GI) tracts of humans and animals In 1906 Dr Metchnikoff described that the long life-spans of people in Bulgaria and the Russian Steppes had were traceable the consumption of large amounts of beneficial bacteria The term, probiotic is used to refer to these beneficial bacteria Many probiotics provide health benefits such as the amelioration of symptoms of antibiotics-induced diarrhea, acute diarrhea, traveler diarrhea, allergies, respiratory and urinary tract infections inflammatory bowel disease, irritable bowel syndrome, colon and bladder cancer, and rheumatoid arthritis. (Doron and Gorbrach, 2006; Goldin and Gorbrach, 2008, and Kaur et al 2009)

2. Description of the Related Art

Since *Bifidobacterium* and *Lactobacillus* were among the first probiotic bacteria described by research scientists to provide health benefits to both animals and humans, they are the most common choices for commercial probiotic products Unfortunately, most of *Bifidobacterium* spp and *Lactobacillus* spp are sensitive to elevated temperatures and/or oxygen exposure (Taiwalkar, Kailasapathy 2004) It is, therefore, often recommended that probiotic products containing *Bifidobacterium* and *Lactobacillus* be stored at cold temperatures and to avoid the term exposure to air These requirements impose substantial challenges to methods for manufacturing such products since, during processes of product manufacture, storage, transportation, and product display, the materials and product are often be exposed to higher temperatures and ambient air.

The ability of *Bacillus* spp to form endospores under unfavorable conditions renders them as naturally heat tolerable lactic acid bacteria. These endospores can maintain bacterial viability under elevated temperature greater than 100° C. *Bacillus subtlis* which are used in many Asian countries can, therefore, be good candidates for inclusion in probiotic products Unfortunately, *Bacillus* spp contain deadly harmful pathogens such as *B. antracis* (anthrax) (Madigan and Martinko, 2005), and *B. cereus* (food poisoning) (Kotiranta et al 2000) There exists, therefore, the potential danger of transferring pathogenic genes from highly pathogenic *B. antracis* or *B. cereus* into probiotic *B. subtlis*.

*Pediococcus* is a beneficial bacteria naturally existing in human and canine gastrointestinal (GI) tracts (Kim Adachi, 2007), and has been used as the starter for the fermentation of human sausage preparations. Unexpectedly, *Pediococcus* can be selected to survive at temperatures up to 65° C. Such selected bacteria are able to grow under both aerobic and semi-aerobic conditions, and, therefore, are much less sensitive to oxygen exposure. More importantly, *Pediococcus* is much less sensitive to stomach acidic environments (Mizutani et al, 2007, Lin and Ishida 2008).

Probiotic products and fermented foods are rapidly growing in importance as the public awareness of their benefits continues to increase Most probiotic products are commercially available as either food or dietary supplements, which seem to be more diverse and active than other areas where probiotics have been used, such as in dairy products The supplements come in many different product formats and contents, including capsules, liquids, tablets, and even food-like formats (Messonnier 2001). In order to accomplish the manufacturing and packaging of these probiotic bacteria, it is very essential to overcome certain industrial challenges such as the typically elevated temperatures and high pressures that are employed during the manufacturing process (Bauser et al 2003). For example, cat, dog and small animal food is usually available as pellets which are manufactured by either baking or a process called, extrusion. During the extrusion process, cut dough or a mixture of raw materials is fed into an expander, while pressurized steam or hot water is added. If extruded kibble is exposed to air for too long or not properly stored, the fats and oils added after cooking can become rancid, and vitamins and minerals in the food may be destroyed by heat during storage or shipping Therefore heat plays a significant role in both the manufacturing processes and also in the storage and transportation of the finished products, making it vital to develop a strain that can withstand such elevated temperatures and high pressures.

In this study, we provide an optimized strain of *Pediococcus acidilactici* (deposited in the Agricultural Research Service (ARS) Patent Culture Collection (International Depositary Authority; 1815 N. University St.; Peoria Ill.; 61604; USA) on May 24, 2011 as NRRL B-50517 and identified as IMPH101) that is viable above 65° C., is able to grow in a pH range between 1 and 6.2, and is also able to grow in aerobic and anaerobic conditions. This will increase both the efficiency of the methods for manufacturing probiotics and the integration of probiotics into food/feed manufacturing processes, which often require high temperatures. In addition, the temperature resistant probiotics can be utilized in conjunction with food or beverages that require high temperatures to prepare such as coffee, tea or hot vegetable/meat soups for human consumption Moreover, these novel bacteria will enable the development of probiotic supplements or functional foods that have the ability to survive extreme conditions such as gastric acid, rigorous temperatures of manufacturing and also have extended shelf-lives. IMPH 101 is representative of strains referred to throughout the specification as IMPH.

SUMMARY OF THE INVENTION

Additional aspects and/or advantages of the invention will be set forth in part in the description which follows and, in part, will be obvious from the description, or may be learned by practice of the invention.

One embodiment of the disclosure comprises a *Pediococcus acidilactici* strain that is viable above 65° C., is able to grow in aerobic and anaerobic conditions, and in a pH range between 1 and 6.2; more particularly, a *Pediococcus acidilactici* strain deposited in the Agricultural Research Service (ARS) Patent Culture Collection as NRRL B-50517.

A further embodiment of the disclosure relates to a method for producing the *Pediococcus acidilactici* strain described above comprising selecting *Pediococcus acidilactici* for tolerance to elevated temperatures, low pH values, and aerobic and anaerobic conditions.

A still further embodiment of the disclosure concerns a product of manufacture comprising the above described

*Pediococcus acidilactici* strain; more particularly, a product comprising a consumable composition of matter.

An additional embodiment of the invention relates to a product of manufacture comprising a probiotic composition for dietary augmentation; more particularly a feed or food.

Another embodiment of the disclosure relates to a method of dietary augmentation, comprising administering to a human or animal a probiotic composition containing the above described *Pediococcus acidilactici* strain.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Preparation of MRS Agar Medium

MRS agar broth and plates were prepared by adding the individual components of the medium to required concentrations, which was made up to 1 liter with de-ionized water The pH was then adjusted as necessary to 6.2 using sodium hydroxide or hydrochloric acid as required (Media composition 2008).

Dilution and Spread Plate Technique

Dilution and plating of samples is a method for determining the number of bacteria present in a particular sample and most importantly to isolate individual colonies. For this study, 0.5 g powder packets of Mitogrow, a commercially available form of the *Pediococcus acidilactici* strain IMPA was taken as a sample and dissolved in 5 ml of 1× Phosphate Buffered Saline (PBS) solution. The solution was then mixed thoroughly by vortex stirring at regular intervals for up to 15 minutes. From this sample, 10 µl of sample was taken and diluted in 990 µl of PBS solution in an Eppendorf tube. This is the $10^{-2}$ dilution of the sample. From the $10^{-2}$ dilution, 10 µl of sample was taken and diluted again in 990 µl of PBS solution, which gives the $10^{-4}$ dilution. This procedure was repeated taking 10 µl from the $10^{-4}$ dilution as a diluent, thus obtaining the $10^{-6}$ dilution From the $10^{-6}$ dilution, 100 µl of sample was taken and diluted in 900 µl of PBS solution to give a dilution of $10^{-7}$. And, finally from the dilution tube, another 100 µl of sample was taken and diluted in 900 µl of PBS solution, to obtain a dilution of $10^{-8}$.

A PBS Tube without any Inoculation of the Sample was Used as a Control

By the above method several dilutions of a sample were obtained, which were then cultured onto a pH 62 MRS agar plate by adding 100 µl from the $10^{-6}$, $10^{-7}$ and $10^{-8}$ tubes and spreading them using glass beads. The plates were incubated at 45° C. for 24 hours, after which the number of colonies can be determined by a direct and viable counting method known as Heterotrophic plate count (Cell Enumeration 2009). In this method, the number of colonies grown were counted and used to estimate the number of bacteria in the initial sample by the following formula:

$$B=N/D$$

Where,
B=number of bacteria
N=number of colonies counted on a plate
D=dilution factor (1, 10, or 100).

High-Temperature Resistant Selection of *P. acidilactici*

Following the above technique, individual colonies were isolated. A single colony was taken using a sterile toothpick and introduced into 5 ml of MRS agar broth in 15 mL falcon tubes. Several individual colonies were introduced into separate tubes in a similar fashion, so as to increase the amount of the starter culture and the chances of isolating a temperature-resistant strain. These tubes were incubated at 65° C. in a Hot Water Bath incubator for 24-48 hours. An incubation time of 24-48 hours was employed in order to establish that there had been survival among the *Pediococcus acidilactici* that came from a single colony. It is also a way of enriching the surviving bacteria in such a way that the ensuing progeny will be more resistant to heat than the previous generation, enhancing the chances of obtaining a strain that is not only resistant to 65° C. but also to even higher temperatures.

To determine whether there had been any growth of *P. acidilactici* in the tubes incubated at 65° C. for 24-48 hours, 100 µl of broth from each tube was cultured onto MRS agar plates by Spread Plate Technique and the number of colonies estimated after incubation at 45° C. overnight. It is also ideal to determine the number of colonies in the initial single colony taken for selection so to estimate the survival rate of the bacteria during the course of the heat treatment and after its completion This was done by culturing 100 µl of broth from the tubes onto MRS agar plates and incubating them at 45° C. for 24 hours, immediately after inoculation into 5 ml of MRS agar broth and also at regular time intervals prior to and during the 24-48 hour period of heat treatment to observe the change in number of cells over time.

If there is any growth, isolated colonies from the MRS agar plates were then introduced again into 5 ml MRS broth tubes and incubated again at 65° C. so as to establish a replicate and also to verify the viability of the bacteria. The same procedure leads to the amplification of the bacteria which can survive at the pre-set temperature. Once the procedure was repeated and colonies were isolated again, the temperature was raised to 70° C. and the experiment was repeated. This process was repeated by increasing the selection temperature until a strain that survived at 85° C. was developed. The strains thus isolated were recorded as IMPA-I, IMPA-2 and so on.

Low-pH Tolerance Selection

The goal of the study was to isolate a strain which is capable of surviving both high temperatures and low pH levels. With this in mind the *Pediococcus acidilactici* strain obtained through temperature resistant selection was used as the starter culture for pH selection. Once selection for temperature resistance was achieved in the form of a desired strain which was capable of surviving at a very high temperature, such as 85° C., single colonies of *Pediococcus acidilactici* obtained through the dilution and spread plate technique was subjected to pH tolerance by inoculating the culture into MRS broths of different pH levels MRS ranging from 1.0 to 6.2.

Similar to the temperature resistance method, the colonies obtained after initial culturing of the 85° C. strain were subjected to subsequent pH selection by inoculating them into a 2.5 pH MRS broth and incubating it at 45° C. for 24 hours. In the case of pH selection, the time of incubation was limited to 24 hours based on previous research results (Lin, 2006). Once the number of colonies was estimated the procedure was repeated again at the same pH level to observe if there is any growth of the microorganism This helped in isolating viable cultures that are tolerant to 2.5 pH levels. A method of enriching the selected strain was to inoculate it in a MRS broth set at a comfortable pH level such as 4.5 and then re-introduce the cultured sample to the pH level of selection, i.e., once colonies survived and grew in 2.5 pH MRS broth, in order to enrich it, the sample was cultured for 24 hours at 4.5 pH MRS broth and then re-selected again at pH 2.5 This method was repeated at a pH level of 1.5 using MRS broth and was very effective in the amplification of *Pediococcus acidilactici* that tolerates pH 1.5.

Preparation of Glycerol Stock

Selected strains of *Pediococcus acidilactici* that survived at the different temperatures, especially IMPH that survived at both 85° C. and pH 1.5 were preserved for further experiments as required. Therefore, it was necessary to establish a method in which to store the viable bacterial cells. One of the techniques widely used is the quick-freezing method, wherein the viable cells are stored at −70° C. after suspending them in a mixture of growth media and a stabilizing protectant such as glycerol. It has been observed that freezing bacteria directly without any protection can cause loss of viability during the freezing and subsequent thawing process due to mechanical and physiological conditions (Morrison 1979). Accordingly, glycerol was used as a protecting agent for the process of freezing.

In order to freeze and store the selected *Pediococcus acidilactici* cultures, first the samples are cultured using the spread plate technique in a 5 ml falcon tube consisting of MRS broth after incubation at 45° C. overnight. It is important that the sample be prepared for freezing after overnight incubation and not 24 hours, since the bacteria in the overnight incubation sample are still in the 'log' phase of the growth curve. This helps in establishing a sample that can readily grow to maximum potential after it is thawed. Subsequent to freezing 300 μl of the sample is taken in a labeled cryogenic tube, to which is added 300 μl of a mixture solution containing 50% MRS broth and 50% glycerol. The mixture solution containing glycerol and MRS broth in equal amounts was prepared using sterile glycerol and MRS broth before the experiment was set up. The cryogenic tube containing the cultured sample of *Pediococcus acidilactici* and the glycerol-MRS broth mixture was thoroughly mixed by vortex and immediately set into dry ice or into the −70° C. freezer to initiate the freezing and storage process. Several cryogenic tubes were set up in similar fashion and hence are termed, 'primary seed'. These tubes can be used as and when required to cultivate the selected strain of *Pediococcus acidilactici*. During the process of preparing glycerol stock 100 μl of the initially cultured sample was diluted and plated onto MRS agar plates for incubation at 45° C. for 24 hours, which is used to compare the survival of the cryogenically frozen samples which were also diluted and plated onto MRS agar plates and incubated at 45° C. for 24 hours. This was used to establish and check if the freezing process affected the survival of the selected strain of *Pediococcus acidilactici* (IMPH) capable of surviving at 85° C. and at a low pH of 1.5

Comparison of Aerobic and Anaerobic Growth Characteristics

Production of probiotics involves certain techniques such as conventional batch fermentation procedures, continuous culture and immobilized cell system technologies (Heller 2001). *Pediococcus acidilactici* are facultative anaerobes that are capable of surviving in the presence and also in the absence of oxygen (Facklam and Elliot 1995). However, for production purposes, it is ideal to identify a strain that produces high yields of culture under both aerobic and anaerobic conditions. In order to determine the most optimal conditions of growth it is necessary to compare the difference in growth characteristics of *Pediococcus acidilactici* with the parent strain, since the ideal strain was obtained from the previous techniques of temperature and pH selection. The strain obtained after the resistance selection methods, which was capable of surviving 85° C. and pH 1.5 was cultured onto MRS agar plates and a single colony was introduced to 25 ml tubes containing MRS agar broth. Another sample of culture was taken from the parent type *Pediococcus acidilactici*, incubated onto MRS agar plates and inoculated into 25 ml MRS tubes as before. Two separate tubes were set up for aerobic and anaerobic testing. The aerobic tube was incubated for 24 hours in an Environmental shaker where the temperature was 45° C. and the speed of shaking set at 250 rpm, in order to induce aeration. Meanwhile, 1 ml of mineral oil was added on top of the broth in the anaerobic tubes and their mouths sealed with tape so as to avoid any discrepancies in the exposure to oxygen or air exchanges. They were incubated for 24 hours in the regular incubator at 45° C. m a still position, so as to avoid aeration.

Growth characteristics of the regular *Pediococcus acidilactici* were also determined by the same procedure using the bacteria from Mitogrow samples, which acts both as a control and a means of comparison between the wild type strain and the strain resistant to temperature and pH. 0.5 g of Mitogrow powder was dissolved into 5 ml of 1×PBS solution, serially diluted and then plated onto MRS agar plates and incubated at 45° C. for 24 hours. A single colony was then subjected to the same treatment of aerobic and anaerobic conditions as discussed above.

At incubation intervals of time, 1 ml of the broth from the tubes was withdrawn and their optical density was measured using a Spectrophotometer set up at 600 nm wavelength. The idea was to measure the amount of light that passes through a liquid culture, to estimate the number of cells/ml based on the amount of light that passes through (Cell Enumeration 2009). This is an indirect and total method to determine not only the growth of *Pediococcus acidilactici* but also can be used to observe any amplification during the procedure.

Physiological Comparison Parent *Pediococcus acidilactici* Strain and Selected Strain of *Pediococcus acidilactici* (IMPH)

Samples from IMPA and ATCC *Pediococcus acidilactici* strain 25743 purchased from American Type Culture Collection (ATCC), Manassas, Va., and the above strain selected for 85° C. and pH 1.5 survival were subjected to temperature tolerance selection and also to pH selection. 10 μl of the sample was suspended into 490 μl of MRS media broth in an eppendorf tube with different pH and incubated at 85° C. up to 24 hours. The number of colonies within the initial inoculated sample was determined by plating 100 μl of broth immediately after inoculation onto MRS agar plates using spread plate technique and incubated at 45° C. for 24 hours. This gives a count of the number of colonies in the starting population before the treatment. After the 85° C. treatment 100 μl from each of the eppendorf tubes was plated on to MRS agar plates. The total number of colonies was counted from the plates after incubating them for 24 hours at 45° C., which gives the number of colonies; an indication of the similarity or difference between the survivability and replicating capabilities of the strains.

Simultaneously, the ATCC 25743 strain, IMPA and the IMPH *Pediococcus acidilactici* strains were inoculated into 1 ml MRS broth taken in eppendorf tubes and subjected to 1.5 pH treatment for the pH tolerance selection This set up provided a confirmatory method and by using the spread plate technique, a quantitative measure of the differences between the wild type and the temperature and pH resistant strains of *Pediococcus acidilactici*. This experiment was replicated three times, so as to establish a set of confirmatory data regarding the comparisons between the number of colonies in the starting population and the number of colonies after the desired treatment of both the wild type and the selected strains of *Pediococcus acidilactici*.

Pilot IMPH *Pediococcus acidilactici* Strain Scale-Up Experiment at 85° C.

Into a set of two 250 µl flasks, 50 µl of MRS broth prepared and sterilized prior to the experiment were placed. To these flasks 100 µl of IMPH primary seed stored at −70° C. was added as inoculum. The flasks were then incubated at 45° C. for 24 hours so as to allow maximum growth of the culture into a large batch of *Pediococcus acidilactici*. From this large batch of sample, 10 ml of sample was extracted and introduced into two separate 15 ml falcon tubes. The tubes containing 10 ml of the sample were then centrifuged for 15 minutes at an rpm of 2500. After centrifugation a pellet is formed at the bottom of the tube while the supernatant remains at the top. The supernatant is discarded and the process is repeated so as to concentrate the pellet. The pellet from each of the tubes is then re-suspended into 2 ml MRS broth and 100 µl of the sample is plated onto MRS agar plates and incubated for 24 hours at 45° C., which is a measure of the initial inoculum and helps in determining the survival rate of *Pediococcus acidilactici* that is subjected to the temperature selection. The tube with the pellet was thoroughly mixed and incubated at 85° C. for 24 hours. After the incubation period the samples were cultured through the dilution and spread plate technique up to $10^{-4}$ dilution and plated onto MRS plates which were incubated at 45° C. for 24 hours.

30 ml remaining from the above mentioned experiment was centrifuged at 2500 rpm for 15 minutes and the pellet thus obtained was concentrated and re-suspended in 2 ml MRS broth. The re-suspended culture solution was then divided into two samples of 1 ml each. Like the previous experiment, the samples incubated at 85° C. $10^{-2}$ dilutions of both the samples were cultured at regular intervals: 0 hour, 1 hour 2 hours and at 4 hours of incubation. The experiments were repeated in order to establish a replicate of the results for accuracy.

16s Ribosomal DNA Typing for Identification of *Pediococcus acidilactici*

16s ribosomal DNA typing was conducted as a confirmatory method in identifying the selected *Pediococcus acidilactici* strain capable of surviving 85° C. and pH 1.5 culture conditions. Several strains were used in the PCR typing process as follows:+

Table 1: Strains Used for 16S rDNA Tying Using PCR

TABLE 1

| Strain Name | PCR Designation |
|---|---|
| IMPA | 1 |
| *Pediococcus acidilactici*, ATCC 25743 | 2 |
| IMHP2.5 (Selected strain of *Pediococcus acidilactici* capable of growth at 85° C. and pH 2.5) | 3 |

TABLE 1-continued

| Strain Name | PCR Designation |
|---|---|
| IMHP (Selected strain of *Pediococcus acidilactici* capable of growth at 85° C. and pH 1.5) | 4 |
| Positive control | +ve |
| Negative control | −ve |

All of the different strains were routinely maintained at 4° C. after growth at optimum temperature for 24 hours on MRS agar plates. Two 16S rDNA primers were used which are capable of adhering to the highly conserved regions of the gene encoding 16S RNA which is conserved among all organisms. The primers used for the typing process are as follows Primer A (360-388) CGGCCCAGACTCCTACGGGAG-GCAGCAG and Primer B (847-822) GCGTGGACTAC-CAGGGTATCTAATCC, which come from well conserved regions among the Eubacteria. In addition to the sequences above, the sequences for "M13" sequencing primers were added to the 5' ends of the primers so that the PCR products can subsequently be sequenced directly without cloning.

A. Preparing Cell Lysate for Template Genomic DNA

A sterile toothpick was used to touch a well-isolated colony obtained on the MRS agar plates and the contaminated end of the toothpick is dipped into the PCR mixture.

B. PCR

'Ready-to-go' PCR tubes were obtained from GE Healthcare Life Sciences, which contain a pre-dispensed mixture of nucleotides, buffer components, $Mg^{+2}$, and Taq polymerase. 24 µl of the 'master mix' containing the 360 and 822 primers in water were added into each tube. The toothpick is dipped into these tubes which are then left on ice so as to avoid the PCR reaction being started prematurely. The tubes were vortexed to mix the reagents and centrifuged for few seconds to bring all the components to the bottom of the tube. Following this, a couple drops of mineral oil were added to the tube, enough to cover the aqueous solution and the tubes were then placed into the thermocycler. The cycling program was as follows 7 minutes 94° C.

35 cycles of 45 seconds 94° C., 30 seconds 55° C., 60 seconds of 72° C.

L0 minutes 72° C.

Hold at 4° C.

C. Gel Electrophoresis

1× buffer solution was prepared by adding 20 ml 50×TAB buffer, which was made by adding 40 mM Tris, 20 mM acetic acid and 1 mM of EDTA with a pH of 8.4 to 980 ml of de-ionized water. 45 ml of 1×TAE buffer was taken in a 250 ml bottle to which agarose was added so as to make it up to 1.5% agarose gel. The solution was heated in a microwave to dissolve the agarose and then cooled at room temperature for 5 minutes, and then the gel was poured into the apparatus. The samples were prepared by mixing 5 µl of the PCR reaction, 4 µl of 1×TAE buffer, and 1 µl of 10× loading buffer. All 10 µl of each sample was loaded into separate wells and 10 µl of 100 bp ladder marker was also loaded into the well at the end. The samples were electrophoresed at ~100 V until the tracking dye reached three quarters of the gel. The gel was then removed and stained for approximately 15 minutes in ethidium bromide to observe for bands under ultraviolet (UV) light.

D. Purification of Sample for Sequencing

Before sequencing, excess primers were removed from the sample by treating the PCR sample with two enzymes, viz. exonuclease I and alkaline phosphatase. These enzymes digest the remaining single-stranded primers but the doublestranded PCR product is resistant to digestion. 10 µl of the PCR product was transferred to a pre-labeled tube and 4 µl of the Exo I/AP mix was added. The tubes were then incubated at 37° C. for 15 minutes for digestion of primers and dNTPs, then at 80° C. for 15 minutes to kill the enzymes. The samples were then sent for sequencing of the obtained, purified PCR product.

E. Analysis

Comparison of the 16S rDNA sequences of the various strains used in the procedure with the large volume of ribosomal database was performed to determine the most closely related organisms Temperature Tolerance Selection From the above mentioned procedure, the MRS plates with viable *Pediococcus acidilactici* colonies obtained after culturing IMPA were used as the starter inocula for the temperature tolerance selection experiment. 8 colonies were randomly selected from the two plates and each was inoculated into 5 ml MRS broth which was incubated at 65° C. for 24 hours. After the incubation period, 100 µl of the sample was plated on MRS agar plates and incubated further at 45° C. 3 out of the 8 samples used had given rise to more colonies as compared to others.

Table 2 of *Pediococcus acidilactici* after Incubation at 65° C.

TABLE 2

| Sample No. | Number of live *Pediococcus acidilactici* (CFU) after incubation at 65° C. |
|---|---|
| IMPA-1 | $4 \times 10^2$ |
| IMPA-2 | $3 \times 10^2$ |
| IMPA-3 | $9 \times 10^2$ |
| IMPA-4 | $8 \times 10^2$ |
| IMPA-5 | $3 \times 10^2$ |
| IMPA-6 | $4 \times 10^2$ |
| IMPA-7 | $2.4 \times 10^3$ |
| IMPA-8 | $2 \times 10^2$ |

From the results obtained sample numbers IMPA-3, IMPA-4 and IMPA-7 were deemed more promising than the others based on the colony morphology such as size when compared to the other colonies surrounding them and also since they were the higher yielding of the selected samples. Each of the colonies thus obtained were further subjected to temperature tolerance selection at 65° C. which demonstrated an increase in the total number of colonies The total number of colony forming units was as below.

Table 3: Number of *Pediococcus acidilactici* Colonies after Reselection at 65° C.

TABLE 3

| Sample No. | Total number of viable *Pediococcus acidilactici* after reselection at 65° C. |
|---|---|
| IMPA-3 | $3.2 \times 10^3$ |
| IMPA-4 | $9.9 \times 10^3$ |
| IMPA-7 | $5.3 \times 10^4$ |

After the reselection of the strain at 65° C., based on the total number of colonies formed by each sample, IMPA-4 and IMPA-7 were observed to be more significant than IMPA-3. Hence, from each of these samples, 5 CFUs were randomly chosen and subjected to the selection process at 70° C. After the incubation on MRS agar plates it was seen that the total number of colony forming units from IMPA-7 at $4.3 \times 10^4$ viable cells was much greater than those of IMPA-4 which had $3.6 \times 10^3$ viable cells during the first cycle.

Since IMPA-7 showed better survival than IMPA-4, IMPA-7 was used for the selection of *Pediococcus acidilactici* at 70° C., 75° C., 80° C. and 85° C. In order to determine their survival and also enrich them, several defined temperature selection cycles were repeated. The best survived bacterial colonies were selected and used for next elevated temperature selection. This method also ensured the restriction of false-positives thereby limiting the possibilities of errors. The survival percentage at each stage was recorded based on $1 \times 10^8$ CFU which is the amount of live *Pediococcus acidilactici* found in a single colony.

Table 4: Total Percentage of *Pediococcus acidilactici* after Temperature Tolerance Selection:

TABLE 4

| Temperature | Number of Selection Cycles | Total Survival Percentage of Final Cycle |
|---|---|---|
| 65° C. | 3 | 2.7% |
| 70° C. | 3 | 3.2% |
| 75° C. | 5 | 11.0% |
| 80° C. | 12 | 24.0% |
| 85° C. | 18 | 47.2% | pH Tolerance Selection

Figure 1:
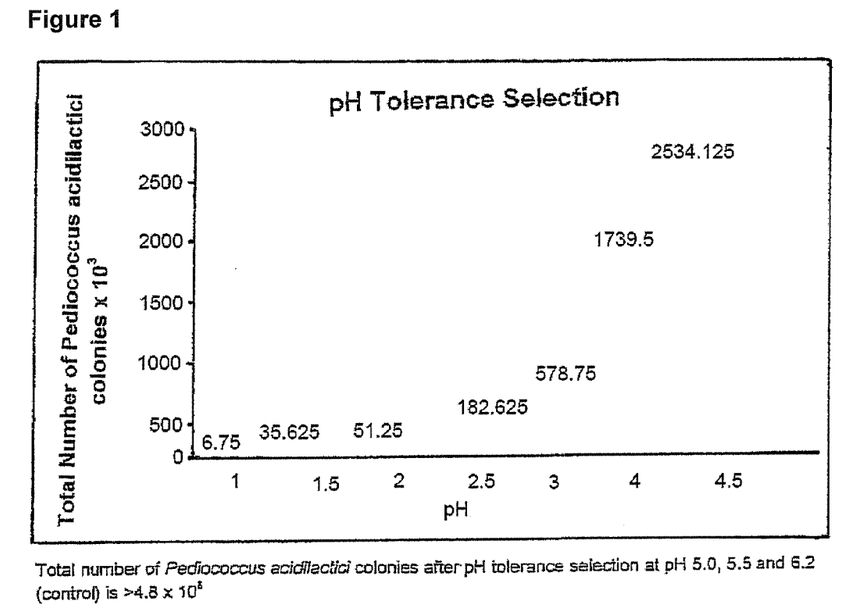
FIG. 1 shows the Total Number of *Pediococcus acidilactici* colonies after selection at 85° C. and pH levels of 1.0, 1.5, 2.0, 2.5, 3.0, 4.0, 4.5, 5.0, 5.5, and 6.2.

The *Pediococcus acidilactici* strain selected through the temperature tolerance method which is capable of survival at 85° C. was renamed as 'IMH', for better understanding in order to trace the origins. IMH strains were used to select for a strain which can survive both high temperature and low pH levels. 10 µl of the IMH sample was inoculated into 5 ml MRS broth at pH levels 1.0, 1.5, 2.0, 2.5, 3.0, 4.0, 4.5, 5.0, 5.5, and 6.2. All of the tubes were incubated at 85° C. for 24 hours and plated using the spread plate technique to determine the number of viable *Pediococcus acidilactici* colonies. There was notable amount of survival in the lower pH levels as demonstrated in the figure below.

FIG. 1: Total Number of *Pediococcus acidilactici* colonies after selection at 85° C. and pH levels of 1.0, 1.5, 2.0, 2.5, 3.0, 4.0, 4.5, 5.0, 5.5, and 6.2.

The survivals of IMH at pH 2.5 were used for a further selection for pH tolerance using MRS broth of pH 2.5. The nomenclature of the pH selected strain was named as 'IMP'. Based on the initial results and colony morphology such as size of the colonies, IMP-1 and IMP-3 were selected. A random selection of 5 colonies of IMP-I and IMP-3 were inoculated into 5 ml MRS of pH 2.5 and incubated at 85° C. for 24 hours. They were then plated onto MRS agar plates after the treatment. The same selected procedures were repeated for 5 separate cycles both to ensure that selection of false-positives was avoided and to enrich the strain.

Table 5: Total Number of *Pediococcus acidilactici* Colonies after Selection at 85° C. and pH2.5

TABLE 5

| Cycle No. of selection at pH 2.5 and 85° C. | Total Number of *Pediococcus acidilactici* | |
|---|---|---|
| | IMP-1 | IMP-3 |
| 1 | $1.1 \times 10^5$ | $7.8 \times 10^4$ |
| 2 | $1.5 \times 10^5$ | $1.1 \times 10^5$ |
| 3 | $2.0 \times 10^5$ | $8.6 \times 10^4$ |

TABLE 5-continued

| Cycle No. of selection at pH 2.5 and 85° C. | Total Number of *Pediococcus acidilactici* | |
|---|---|---|
| | IMP-1 | IMP-3 |
| 4 | $5.1 \times 10^5$ | $3.3 \times 10^5$ |
| 5 | $4.0 \times 10^5$ | $6.4 \times 10^5$ |

The results obtained above established the tolerance of the strain for pH2.5 and 85° C., which provided further impetus to push the strain to the extreme lower limit of pH 1.5. Using the similar procedure after the MRS broth was replaced with the 1.5 pH media, the selection process continued at 85° C. and pH 1.5. IMP-1 and IMP-3 from the earlier pH tolerance selection were used as initial inocula and the experiment was repeated for 7 cycles.

Cycle 1 to cycle 4 yielded low numbers of colonies, while cycles 5 through 7 demonstrated a higher resistance and growth capability in IMP-1. On the other hand, IMP-3 was consistently lower when compared to the former. The results of this experiment are set forth in Table 6.

Table 6 Total Number of *Pediococcus acidilactici* Colonies after Selection at 85° C. and pH 1.5

TABLE 6

| Cycle No. of selection at pH 1.5 and 85° C. | Total Number of *Pediococcus acidilactici* | |
|---|---|---|
| | IMP-1 | IMP-3 |
| 1 | $1.7 \times 10^4$ | $2.6 \times 10^4$ |
| 2 | $2.1 \times 10^4$ | $4.7 \times 10^4$ |
| 3 | $7.7 \times 10^4$ | $3.8 \times 10^4$ |
| 4 | $9.3 \times 10^4$ | $1.2 \times 10^5$ |
| 5 | $2.9 \times 10^5$ | $1.3 \times 10^4$ |
| 6 | $3.6 \times 10^5$ | $8.7 \times 10^4$ |
| 7 | $2.9 \times 10^5$ | $4.5 \times 10^4$ |

An efficient strain capable of surviving both low pH and high temperature was obtained as described in Table 6. The final strain obtained after both temperature tolerance and pH tolerance selection, which was capable of surviving 85° C. and pH 1.5, was given a final designation as 'P'. A glycerol stock of IMPH was prepared and stored at −70° C.

Physiological Comparison Between *Pediococcus acidilactici* IMPA, ATCC 25743 Strains and Selected Strain Resistant to 85° C. and pH 1.5 (IMPH)

In order to confirm that the selected strain of *Pediococcus acidilactici* is capable of both survival and replication, it is necessary to perform certain experiments outlining the difference between the parent and the selected strain. At first, an API-50-CHL Bacteria Identification System (Fisher Scientific, New Jersey) was used to establish that the selected strain is *Pediococcus acidilactici*. After this, it became prudent to demonstrate the differences between the parent strain and IMPH.

*Pediococcus acidilactici* ATCC 25743 strain obtained from ATCC together with IMPA as controls, and IMPH were analyzed using the API 50 CHL test to characterize and identify the bacteria based on the utilization of proteins, carbohydrates, minerals and other components essential for growth. As per the standard protocol for the API test, the test strips were inoculated and incubated at 37° C. for 48 hours. The changes in color in the test strips were observed at the 24-hour mark and the readings were recorded as positive, partially positive and negative reaction. After the 48 hour incubation period, the changes in color were noted again and the results compared against the standard to identify the microorganism.

Based on the results obtained it was established that all three samples, viz ATCC strain 25743, IMPA and IMHP were *Pediococcus acidilactici*.

Table 7 API 50 CHL Identification

TABLE 7

| API 50 CHL | Standard *Pediococcus acidilactici* | ATCC | IMPA | IMHP |
|---|---|---|---|---|
| Control | | | | |
| Glycerol | | | | |
| Erythritol | | | | |
| D-Arabinose | | | | |
| L-Arabinose | 100 | − | + | − |
| D-Ribose | 100 | − | − | + |
| D-Xylose | 100 | − | + | + |
| L-Xylose | | | | |
| D-Adonital | | | | |
| Methyl β-D-Xylopyranoside | | | | |
| D-Galactose | 100 | − | + | + |
| D-Glucose | 100 | − | + | + |
| D-Fructose | 100 | − | + | + |
| D-Mannose | 100 | − | + | + |
| L-Sorbose | | | | |
| L-Rhamnose | 75 | − | + | + |
| Dulcitol | | | | |
| Inositol | | | | |
| D-Mannitol | | | | |
| D-Sorbitol | | | | |
| Methyl-α-D-mannopyranoside | | | | |
| Methyl-a-D-Glucopyranoside | | | | |
| N-Acetylglucosamine | 100 | − | + | + |
| Amygdalin | | | | |
| Arbutin | 50 | − | + | + |
| Esculin ferric citrate | 100 | − | + | + |
| Salicin | 75 | − | + | + |
| D-Cellobiose | 100 | − | + | + |
| D-Maltose | | | | |
| D-Lactose (bovine orgin) | | | | |
| D-Melibiose | | | | |
| D-Sacchariose (sucrose) | | | | |
| D-Trehalose | 75 | + | − | + |
| Inulin | | | | |
| D-MeleZitose | | | | |
| D-Raffinose | | | | |
| Amidon (Starch) | | | | |
| Glycogen | | | | |
| Xylitol | | | | |
| Gentiobiose | 100 | − | − | + |
| D-Turanose | | | | |
| D-Lyxose | | | | |
| D-Tagatose | 100 | − | + | + |
| D-Fucose | | | | |
| L-Fucose | | | | |
| D-Arabitol | | | | |
| L-Arabitol | | | | |
| Potassium Gluconate | − | − | − | |
| Potassium 2-KetoGluconate | | | | |
| Potassium 5-KetoGluconate | | | | |

Standard based on % of positive reaction after 48 hrs. (±6 hrs) at 36° C. ± 2° C.

Once the API test was completed, the samples were subjected to a first set of heat treatment at 85° C. for 24 hours. After the incubation period, IMPA and IMPH strains were plated onto MRS agar and the bacterial colonies were obtained from overnight incubation at 45° C. The same process was repeated for 3 cycles ensuring confirmation of the results. It was observed that during each cycle at 85° C., there was greater than 500-fold difference of bacterial survival between IMPH and IMPA. Survival percentages for IMHP and IMPA were calculated using the initial viable colony count obtained from a single colony. The total number of viable cells in the initial inoculum was $1.2 \times 10^8$ and $1 \times 10^8$ for IMPH and IMPA respectively.

Table 8 Survival Percentage of *Pediococcus acidilactici* Colonies after Selection at 85° C. For Comparison

TABLE 8

| Cycle No. | Survival percentage of *Pediococcus acidilactici* Colonies at 85° C. | |
| --- | --- | --- |
|  | IMHP | IMPA |
| 1 | 23% | .0024% |
| 2 | 25% | .0006% |
| 3 | 32% | .0001% |

The results thus obtained are indicative of the viable cells of *Pediococcus acidilactici* found in IMPA and IMPH strains after high temperature treatment. From the above-formed colony forming units, 122 individual colonies from the IMPA and the IMHP plates were subjected to 85° C. treatment. Each bacterial colony was re-suspended in 500 µl MRS broth and incubated at 85° C. Subsequent to the incubation period of 24 hours, each sample was streaked onto MRS agar plates. They were further incubated for 24 hours at 45° C. The total percentage of survival among the individual colonies of the control IMPA was 8.2% and of the selected strain, IMHP, was 100% (Table 9).

Table 9 Comparison Between IMPA and Selected IMPH *Pediococcus acidilactici* Strains after 85° C. after $2^{nd}$ Cycle.

TABLE 9

| Sample Used | Total No. of Colony Forming Units Used | Total No. of survival after incubation at 85° C. | Percentage of Survival after $2^{nd}$ cycle |
| --- | --- | --- | --- |
| IMPA | 122 | 10 | 8.2% |
| IMHP | 122 | 122 | 100% |

Upon completion of the temperature survivability comparison, the two samples of *Pediococcus acidilactici*, viz. IMPA and IMPH strains were subjected to comparison tests at pH 1.5. The experiment, which was performed using a triple replicate standard, established a significant difference in the survival capability of IMPA, and that of IMPH. The number of colonies observed after the pH comparison test was recorded as the following table indicates.

Table 10 Comparison Between IMPA and IMPH Strains after pH 1.5 Treatment

TABLE 10

| Replicate No. | Number of *Pediococcus acidilactici* Colony Forming Units (CFU) at pH 1.5 | |
| --- | --- | --- |
|  | IMHP | IMPA |
| 1 | $5.8 \times 10^5$ | $4.0 \times 10^3$ |
| 2 | $4.8 \times 10^5$ | $2.0 \times 10^3$ |
| 3 | $5.3 \times 10^5$ | $7.0 \times 10^3$ |

After the pH survivability results were obtained, each of the samples was cultured at regular growth conditions on MRS agar plates. From the cultured plates, a random selection of colonies was used to determine the survival percentage of individual colonies at pH 1.5 similar to the test for the temperature selection. A total of 120 colonies for each sample taken in eppendorf tubes were subjected to pH 1.5 MRS broths. After 24 hours incubation, each tube was plated onto MRS agar plates. After observing growth from the plated plates after 45° C. incubation, the survival percentage of each sample was determined by the number of colony forming units obtained after the pH treatment. They were as follows:

Table 11 Survival Percentage Comparison Between IMPA, IMPH Strains after pH 1.5 Treatments

TABLE 11

| Sample Used | Total No. of Colony Forming Units Used | Total No. of Survival | Percentage of Survival |
| --- | --- | --- | --- |
| IMPA | 120 | 19 | 15.8% |
| IMHP | 120 | 96 | 80% |

Comparison of Aerobic and Anaerobic Growth Characteristics of IMPH

Figure 2:
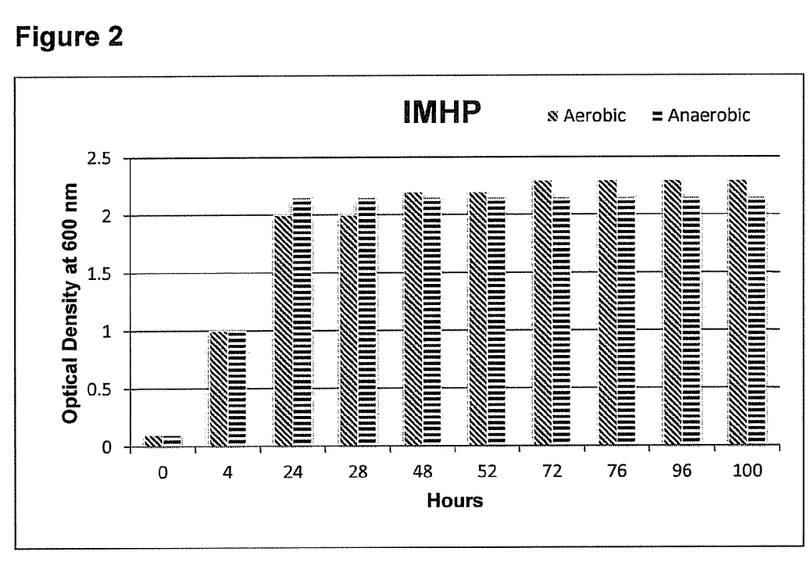
FIG. 2 shows the difference of Aerobic vs. Anaerobic growth characteristics of IMHP.

Using spectrophotometric methods, the optical density of the selected strain of *Pediococcus acidilactici* IMPH was determined at 600 nm after setting up the organism to grow under both aerobic and nearly anaerobic conditions. There was no significant difference between the two growth conditions, though the aerobic conditions of growth seem slightly better when compared to the anaerobic conditions.

FIG. 4 Aerobic Vs. Anaerobic Growth Characteristics of IMPH.

IMPH *Pediococcus acidilactici* Scale-Up Experiment at 85° C.

A pilot batch of the selected IMPH strain of *Pediococcus acidilactici* was grown to determine the stability and the capability of the strain to grow in large quantities which would be essential for commercialization. For the experiment, the IMHP strain was grown in 50 ml MRS broth for 24 hours by incubating it at 45° C. Duplicate bacterial stocks of IMPH, viz. IMPH-A and IMPH-B were used for this experiment. The initial inoculum prior to the treatment was determined by culturing 100 µl of IMPH-A and IMPH-B on MRS agar plates and was standardized at 4 $8 \times 10^5$ CFU/mL for further experiments. After this determination, IMPH-A and IMPH-B were subjected to heat treatment at 85° C. and plated at random time intervals to determine their stability. The MRS plates were incubated at 45° overnight.

The total number of colonies obtained from IMPH-A and IMPH-B showed a decrease in the total number of colonies after 1 hour of incubation, which, however, started to increase at the 2-hour mark and almost doubled at the 4-hour mark in the case of IMPH-B In the case of IMPH-A, the increase is quite evident at the 2-hour mark.

Table 12 Pilot Scale-Up Growth of IMPH Strain

TABLE 12

| Sample | Survival Percentage after incubation at 85° C. | | |
| --- | --- | --- | --- |
|  | 1 hour | 2 hours | 4 hours |
| IMHP-A | 58.3% | 79.1% | 75.0% |
| IMHP-B | 70.8% | 75.0% | 150% |

For this experiment, the same initial inoculum as the above procedure was established since the sample was taken from the original stock solution prepared prior to the test in a 250 mL flask. Therefore, the initial inoculum was $4.8 \times 10^5$ CFU/mL. After incubating the samples in boiling water and 90° C. hot water for 10 minutes, the samples were plated as described previously onto MRS agar plates and incubated at 45° C. for 24 hours. The results of the boiling water were $3 \times 10^2$ and $2.4 \times 10^3$ colony forming units observed in IMPH-A and IMPH-B respectively for the boiling water treatment. For the 90° C. hot water treatment, the two samples showed $7.3 \times 10^3$ and $1.6 \times 10^4$ growth of colony forming units, respectively. These results indicate that the IMPH strain is able to survive even at or close to boiling temperatures.

Table 13 IMPH Growth after Boiling and 90° C. Hot Water Treatment

TABLE 13

| Sample | Total Number of *Pediococcus acidilactici* colonies after treatment | |
|---|---|---|
| | With Boiling Water | With 90° C. hot water |
| IMHP-A | $3 \times 10^2$ | $7.3 \times 10^3$ |
| IMHP-B | $2.4 \times 10^3$ | $1.6 \times 10^4$ |

16S Ribosomal DNA Typing for Identification of *Pediococcus acidilactici*

Though bacteria can be identified with phenotypic identification methods, 16S ribosomal DNA (rDNA)-based identification of bacteria offers a useful and very accurate alternative. Unlike phenotypic identification, which can be modified by the variability of expression of characters, 16S rDNA sequencing provides unambiguous data even for rare isolates. The increase in accurate 16s rDNA sequences and development of targeted primer sequences further underlines the importance and usefulness of molecular identification of bacteria (Olive and Bean 1999).

After the *Pediococcus acidilactici* IMPH strain which can survive at 85° C. and pH 1.5 was selected 16S ribosomal DNA typing was performed to confirm IMPH is *Pediococcus acidilactici*. Bacterial 16S ribosomal DNAs of *Pediococcus acidilactici* IMPH, IMPH 2.5 (*Pediococcus acidilactici* strain capable of survival at both 85° C. and pH2.5), IMPA (the parent strain of IMPH and IMPH 2.5) and the ATCC *Pediococcus acidilactici* strain 25743 were amplified using a conventional PCR technique and specific 16S ribosomal DNA sequence primers, followed by direct DNA sequencing of the amplified 16S ribosomal DNA.

Both sense and antisense DNA sequences obtained were analyzed using an alignment program, CLUSTALW.

Using the sequences obtained, the alignment for the forward and reverse sequences of the samples was as follows:

```
Forward Sequences:
IMPA       -CGGNNCATTTC--GTAG-CAGCAGTAGGGA-TCTTCCACAATGGACGCAAGTCTGATGG  55
ATCC25743  -CGGCCCACTTTAGGAGG-CAGCAGTAGGGA-TCTTCCACAATGGACGCAAGTCTGATGG  57
IMHP2.5    -NNNCCATCATAGGGTAG-CAGCAGTAGGGA-TCTTCCACAATGGACGCAAGTCTGATGG  57
IMHP       GGGGCTCCTATCGGGAAGGCAGCAGTAGGGAATCTTCCACAATGGACGCAAGTCTGATGG  60
            *   *  *  *********  ************************************

IMPA       AGCAACGCCGCGTGAGTGAAGAAGGGTTTCGGCTCGTAAAGCTCTGTTGTTAAAGAAGAA  115
ATCC25743  AGCAACGCCGCGTGAGTGAAGAAGGGTTTCGGCTCGTAAAGCTCTGTTGTTAAAGAAGAA  117
IMHP2.5    AGCAACGCCGCGTGAGTGAAGAAGGGTTTCGGCTCGTAAAGCTCTGTTGTTAAAGAAGAA  117
IMHP       AGCAACGCCGCGTGAGTGAAGAAGGGTTTCGGCTCGTAAAGCTCTGTTGTTAAAGAAGAA  120
            ************************************************************

IMPA       CGTGGGTGAGAGTAACTGTTCACCCAGTGACGGTATTTAACCAGAAAGCCACGGCTAACT  175
ATCC25743  CGTGGGTGAGAGTAACTGTTCACCCAGTGACGGTATTTAACCAGAAAGCCACGGCTAACT  177
IMHP2.5    CGTGGGTGAGAGTAACTGTTCACCCAGTGACGGTATTTAACCAGAAAGCCACGGCTAACT  177
IMHP       CGTGGGTGAGAGTAACTGTTCACCCAGTGACGGTATTTAACCAGAAAGCCACGGCTAACT  180
            ************************************************************

IMPA       ACGTGCCAGCAGCCGCGGTAATACGTAGGTGGCAAGCGTTATCCGGATTTATTGGGCGTA  235
ATCC25743  ACGTGCCAGCAGCCGCGGTAATACGTAGGTGGCAAGCGTTATCCGGATTTATTGGGCGTA  237
IMHP2.5    ACGTGCCAGCAGCCGCGGTAATACGTAGGTGGCAAGCGTTATCCGGATTTATTGGGCGTA  237
IMHP       ACGTGCCAGCAGCCGCGGTAATACGTAGGTGGCAAGCGTTATCCGGATTTATTGGGCGTA  240
            ************************************************************

IMPA       AAGCGAGCGCAGGCGGTCTTTTAAGTCTAATGTGAAAGCCTTCGGCTCAACCGAAGAAGT  295
ATCC25743  AAGCGAGCGCAGGCGGTCTTTTAAGTCTAATGTGAAAGCCTTCGGCTCAACCGAAGAAGT  297
IMHP2.5    AAGCGAGCGCAGGCGGTCTTTTAAGTCTAATGTGAAAGCCTTCGGCTCAACCGAAGAAGT  297
IMHP       AAGCGAGCGCAGGCGGTCTTTTAAGTCTAATGTGAAAGCCTTCGGCTCAACCGAAGAAGT  300
            ************************************************************

IMPA       GCATTGGAAACTGGGAGACTTGAGTGCAGAAGAGGACAGTGGAACTCCATGTGTAGCGGT  355
ATCC25743  GCATTGGAAACTGGGAGACTTGAGTGCAGAAGAGGACAGTGGAACTCCATGTGTAGCGGT  357
IMHP2.5    GCATTGGAAACTGGGAGACTTGAGTGCAGAAGAGGACAGTGGAACTCCATGTGTAGCGGT  357
IMHP       GCATTGGAAACTGGGAGACTTGAGTGCAGAAGAGGACAGTGGAACTCCATGTGTAGCGGT  360
            ************************************************************

IMPA       GAAATGCGTAGATATATGGAAGAACACCAGTGGCGAAGGCGGCTGTCTGGTCTGTAACTG  415
ATCC25743  GAAATGCGTAGATATATGGAAGAACACCAGTGGCGAAGGCGGCTGTCTGGTCTGTAACTG  417
IMHP2.5    GAAATGCGTAGATATATGGAAGAACACCAGTGGCGAAGGCGGCTGTCTGGTCTGTAACTG  417
IMHP       GAAATGCGTAGATATATGGAAGAACACCAGTGGCGAAGGCGGCTGTCTGGTCTGTAACTG  420
            ************************************************************

IMPA       ACGCTGAGGCTCGAAAGCATGGGTAGCGAACAGGATTAGATACCCTGGTAGTCCACGCCA  475
ATCC25743  ACGCTGAGGCTCGAAAGCATGGGTAGCGAACAGGATTAGATACCCTGGTAGTCCACGCCA  477
IMHP2.5    ACGCTGAGGCTCGAAAGCATGGGTAGCGAACAGGATTAGATACCCTGGTAGTCCACGCCA  477
IMHP       ACGCTGAGGCTCGAAAGCATGGGTAGCGAACAGGATTAGATACCCTGGTAGTCCACGCCA  480
            ************************************************************
```

-continued

```
IMPA        TGGTCATAGCCTGTTTCCCGCACTTCAGGCGGTTGAGCCGAAAGGCTTTCACATTAGACT 535
ATCC25743   TGGTCATAGC-TGTTTCCA------------------------------------------ 495
IMHP2.5     TGGTCATAGC-TGTTTC-------------------------------------------- 493
IMHP        TGGTCATAGC-TGTTTC-------------------------------------------- 496
            ********** ******

Reverse Sequences:
IMPA        -GGGGATAAATG--TACTAATC-TGTTCGCTACCCATGCTTTCGAGCCTCAGCGTCAGTT 56
ATCC25743   -GNGGAATTATG--TTCTAATCCTGTTCGCTACCCATGCTTTCGAGCCTCAGCGTCAGTT 57
IMHP2.5     AGNNGACTTCGGGATTCTAATCCTGTTCGCTACCCATGCTTTCGAGCCTCAGCGTCAGTT 60
IMHP        -GGGGACCCAGC--TACTA-TCCTGTTCGCTACCCATGCTTTCGAGCCTCAGCGTCAGTT 56
              *  **        * *** **  ************************************

IMPA        ACAGACCAGACAGCCGCCTTCGCCACTGGTGTTCTTCCATATATCTACGCATTTCACCGC 116
ATCC25743   ACAGACCAGACAGCCGCCTTCGCCACTGGTGTTCTTCCATATATCTACGCATTTCACCGC 117
IMHP2.5     ACAGACCAGACAGCCGCCTTCGCCACTGGTGTTCTTCCATATATCTACGCATTTCACCGC 120
IMHP        ACAGACCAGACAGCCGCCTTCGCCACTGGTGTTCTTCCATATATCTACGCATTTCACCGC 116
            ************************************************************

IMPA        TACACATGGAGTTCCACTGTCCTCTTCTGCACTCAAGTCTCCCAGTTTCCAATGCACTTC 176
ATCC25743   TACACATGGAGTTCCACTGTCCTCTTCTGCACTCAAGTCTCCCAGTTTCCAATGCACTTC 177
IMHP2.5     TACACATGGAGTTCCACTGTCCTCTTCTGCACTCAAGTCTCCCAGTTTCCAATGCACTTC 180
IMHP        TACACATGGAGTTCCACTGTCCTCTTCTGCACTCAAGTCTCCCAGTTTCCAATGCACTTC 176
            ************************************************************

IMPA        TTCGGTTGAGCCGAAGGCTTTCACATTAGACTTAAAAGACCGCCTGCGCTCGCTTTACGC 236
ATCC25743   TTCGGTTGAGCCGAAGGCTTTCACATTAGACTTAAAAGACCGCCTGCGCTCGCTTTACGC 237
IMHP2.5     TTCGGTTGAGCCGAAGGCTTTCACATTAGACTTAAAAGACCGCCTGCGCTCGCTTTACGC 240
IMHP        TTCGGTTGAGCCGAAGGCTTTCACATTAGACTTAAAAGACCGCCTGCGCTCGCTTTACGC 236
            ************************************************************

IMPA        CCAATAAATCCGGATAACGCTTGCCACCTACGTATTACCGCGGCTGCTGGCACGTAGTTA 296
ATCC25743   CCAATAAATCCGGATAACGCTTGCCACCTACGTATTACCGCGGCTGCTGGCACGTAGTTA 297
IMHP2.5     CCAATAAATCCGGATAACGCTTGCCACCTACGTATTACCGCGGCTGCTGGCACGTAGTTA 300
IMHP        CCAATAAATCCGGATAACGCTTGCCACCTACGTATTACCGCGGCTGCTGGCACGTAGTTA 296
            ************************************************************

IMPA        GCCGTGGCTTTCTGGTTAAATACCGTCACTGGGTGAACAGTTACTCTCACCCACGTTCTT 356
ATCC25743   GCCGTGGCTTTCTGGTTAAATACCGTCACTGGGTGAACAGTTACTCTCACCCACGTTCTT 357
IMHP2.5     GCCGTGGCTTTCTGGTTAAATACCGTCACTGGGTGAACAGTTACTCTCACCCACGTTCTT 360
IMHP        GCCGTGGCTTTCTGGTTAAATACCGTCACTGGGTGAACAGTTACTCTCACCCACGTTCTT 356
            ************************************************************

IMPA        CTTTAACAACAGAGCTTTACGAGCCGAAACCCTTCTTCACTCACGCGGCGTTGCTCCATC 416
ATCC25743   CTTTAACAACAGAGCTTTACGAGCCGAAACCCTTCTTCACTCACGCGGCGTTGCTCCATC 417
IMHP2.5     CTTTAACAACAGAGCTTTACGAGCCGAAACCCTTCTTCACTCACGCGGCGTTGCTCCATC 420
IMHP        CTTTAACAACAGAGCTTTACGAGCCGAAACCCTTCTTCACTCACGCGGCGTTGCTCCATC 416
            ************************************************************

IMPA        AGACTTGCGTCCATTGTGGAAGATTCCCTACTGCTGCCTCCCGTAGGAGTCTGGGCCGAC 476
ATCC25743   AGACTTGCGTCCATTGTGGAAGATTCCCTACTGCTGCCTCCCGTAGGAGTCTGGGCCGAC 477
IMHP2.5     AGACTTGCGTCCATTGTGGAAGATTCCCTACTGCTGCCTCCCGTAGGAGTCTGGGCCGAC 480
IMHP        AGACTTGCGTCCATTGTGGAAGATTCCCTACTGCTGCCTCCCGTAGGAGTCTGGGCCGAC 476
            ************************************************************

IMPA        TGGCCGTC-GTTTTAC-- 491
ATCC25743   TGGCCGTCCGTTTTACA- 494
IMHP2.5     TGGCCGTC-GTTTTACAA 497
IMHP        TGGCCGTCCGTTATACA- 493
            ********  *** ***
```

Based on the alignment, it was observed that all the sequences of *Pediococcus acidilactici* obtained from IMPH and the selection process were very similar and were also identified as *Pediococcus acidilactici*. The positive control for the PCR procedure used as a means of determining the validity of the results and to avoid false-positives was identified as *Escherichia coli*, while the negative control which was an un-inoculated PCR tube with reagents did not produce any sequence.

Table 14 Identification of Sequences Using Ribosomal Database Project

TABLE 14

| Strain Name | Ribosomal Database Project Homologous Sequence Identification Organism |
|---|---|
| IMPA | *Pediococcus acidilactici* |
| *Pediococcus acidilactici*, ATCC#25743 | *Pediococcus acidilactici* |
| IMHP 2.5 | *Pediococcus acidilactici* |
| IMHP | *Pediococcus acidilactici* |
| Positive PCR control | *Escherichia cali* |
| Negative PCR control | ve |

Once the sequences were obtained, their homologous sequences were determined using the Ribosomal Database Project available through the Michigan State University website. It was found that all sequences except the controls showed a high frequency match and were identified as *Pediococcus acidilactici*. The positive control was identified as *Escherichia coli*, while the negative control had no sequence. This established that the strain selected through the rigorous temperature and pH selection procedures was *Pediococcus acidilactici*.

Table 15. Multiplication of *P. acidilactici* IMPH at Different High Temperatures.

TABLE 15

| | Growth Temperature | | |
|---|---|---|---|
| Incubation time | 50° C. | 52° C. | 55° C. |
| 0 | $4.3 \times 10^9$ | $4.3 \times 10^9$ | $4.3 \times 10^9$ |
| 18 hours | $5.4 \times 10^{12}$ | $5.3 \times 10^{12}$ | $.8 \times 10^{12}$ |

Transfer 100 μl of *P. acidilactici* IMPH from the stocks stored at −70° C. freezer to 5 ml MRS broth. Mixed thoroughly, and incubated at 50° C., 52° C. and 55° C. for 18 hours. The total viable cell counts were performed as the followings: for 0 incubation time, performed tenfold series from the IMPH in 5 ml MRS broth right after transferred IMPH from the freezer stocks, and plated 100 μl of diluted MRS broth with *P. acidilactici* IMPH onto MRS plates, and incubated at 45 C for 18 hours. Similarly, after 18 hours incubation, performed series of dilution from the overnight cultures of 50° C., 52° C. and 55° C. separately, and plated 100 μl of diluted MRS broth with *P. acidilactici* IMPH onto MRS plates, and incubated at 45 C for 18 hours. Count the individual colonies on the MRS plates after overnight incubation.

Results:

*P. acidilactici* IMPH is able to multiple more than 880 folds after overnight incubation at 50° C., 52° C. and 55° C. The results demonstrate *P. acidilactici* IMPH can not only can survive at high temperatures but also can multiply the temperatures greater than 50° C.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A *Pediococcus acidilactici* strain that is viable at temperatures between 75° C. and 85° C. while in a pH range between 1 and 4.0 and is able to grow in aerobic and anaerobic conditions deposited in the Agricultural Research Service (ARS) Patent Culture Collection as NRRL B-50517.

2. A *Pediococcus acidilactici* strain of claim 1 that is viable at a temperature between 80° C. and 85° C.

3. A *Pediococcus acidilactici* strain of claim 1 that is viable at a pH≤3.

4. A method comprising: incubating *Pediococcus acidilactici* under conditions that impart resistance to temperatures between 75° C. and 85° C. while in a pH range between 1 and 4.0 and impart the ability to grow in aerobic and anaerobic conditions.

5. A product of manufacture comprising the *Pediococcus acidilactici* strain of claim 1.

6. The product of claim 5 comprising a consumable composition of matter.

7. The product of claim 6 comprising a probiotic composition for dietary augmentation.

8. The product of claim 6 comprising a feed or food.

9. A method of dietary augmentation, comprising administering to a human or animal a probiotic composition containing the *Pediococcus acidilactici* strain of claim 1.

10. A biologically pure culture of the *Pediococcus acidilactici* strain of claim 1.

* * * * *

SEQUENCE LISTING

<160> NUMBER OF SEQ ID NOS: 2

<210> SEQ ID NO 1
<211> LENGTH: 2019
<212> TYPE: DNA
<213> ORGANISM: Artificial Sequence
<220> FEATURE:
<223> OTHER INFORMATION: ATCC 25743
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (113)..(115)
<223> OTHER INFORMATION: n is a, c, g, or t

<400> SEQUENCE: 1

```
cggnncattt cgtagcagca gtagggatct tccacaatgg acgcaagtct gatggcggcc      60
cactttagga ggcagcagta gggatcttcc acaatggacg caagtctgat ggnnnccatc     120
atagggtagc agcagtaggg atcttccaca atggacgcaa gtctgatggg gggctcctat     180
cgggaaggca gcagtaggga atcttccaca atggacgcaa gtctgatgga gcaacgccgc     240
gtgagtgaag aagggtttcg gctcgtaaag ctctgttgtt aaagaagaaa gcaacgccgc     300
gtgagtgaag aagggtttcg gctcgtaaag ctctgttgtt aaagaagaaa gcaacgccgc     360
```

```
gtgagtgaag aagggtttcg gctcgtaaag ctctgttgtt aaagaagaaa gcaacgccgc      420
gtgagtgaag aagggtttcg gctcgtaaag ctctgttgtt aaagaagaac gtgggtgaga      480
gtaactgttc acccagtgac ggtatttaac cagaaagcca cggctaactc gtgggtgaga      540
gtaactgttc acccagtgac ggtatttaac cagaaagcca cggctaactc gtgggtgaga      600
gtaactgttc acccagtgac ggtatttaac cagaaagcca cggctaactc gtgggtgaga      660
gtaactgttc acccagtgac ggtatttaac cagaaagcca cggctaacta cgtgccagca      720
gccgcggtaa tacgtaggtg gcaagcgtta tccggattta ttgggcgtaa cgtgccagca      780
gccgcggtaa tacgtaggtg gcaagcgtta tccggattta ttgggcgtaa cgtgccagca      840
gccgcggtaa tacgtaggtg gcaagcgtta tccggattta ttgggcgtaa cgtgccagca      900
gccgcggtaa tacgtaggtg gcaagcgtta tccggattta ttgggcgtaa agcgagcgca      960
ggcggtcttt taagtctaat gtgaaagcct tcggctcaac cgaagaagta agcgagcgca     1020
ggcggtcttt taagtctaat gtgaaagcct tcggctcaac cgaagaagta agcgagcgca     1080
ggcggtcttt taagtctaat gtgaaagcct tcggctcaac cgaagaagta agcgagcgca     1140
ggcggtcttt taagtctaat gtgaaagcct tcggctcaac cgaagaagtg cattggaaac     1200
tgggagactt gagtgcagaa gaggacagtg gaactccatg tgtagcggtg cattggaaac     1260
tgggagactt gagtgcagaa gaggacagtg gaactccatg tgtagcggtg cattggaaac     1320
tgggagactt gagtgcagaa gaggacagtg gaactccatg tgtagcggtg cattggaaac     1380
tgggagactt gagtgcagaa gaggacagtg gaactccatg tgtagcggtg aaatgcgtag     1440
atatatggaa gaacaccagt ggcgaaggcg gctgtctggt ctgtaactgg aaatgcgtag     1500
atatatggaa gaacaccagt ggcgaaggcg gctgtctggt ctgtaactgg aaatgcgtag     1560
atatatggaa gaacaccagt ggcgaaggcg gctgtctggt ctgtaactgg aaatgcgtag     1620
atatatggaa gaacaccagt ggcgaaggcg gctgtctggt ctgtaactga cgctgaggct     1680
cgaaagcatg ggtagcgaac aggattagat accctggtag tccacgccaa cgctgaggct     1740
cgaaagcatg ggtagcgaac aggattagat accctggtag tccacgccaa cgctgaggct     1800
cgaaagcatg ggtagcgaac aggattagat accctggtag tccacgccaa cgctgaggct     1860
cgaaagcatg ggtagcgaac aggattagat accctggtag tccacgccat ggtcatagcc     1920
tgtttcccgc acttcaggcg gttgagccga aaggctttca cattagactt ggtcatagct     1980
gtttccatgg tcatagctgt ttctggtcat agctgtttc                            2019

<210> SEQ ID NO 2
<211> LENGTH: 1975
<212> TYPE: DNA
<213> ORGANISM: Artificial Sequence
<220> FEATURE:
<223> OTHER INFORMATION: ATCC 25743
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t

<400> SEQUENCE: 2
ggggataaat gtactaatct gttcgctacc catgctttcg agcctcagcg tcagttgngg       60
aattatgttc taatcctgtt cgctacccat gctttcgagc ctcagcgtca gttagnngac      120
ttcgggattc taatcctgtt cgctacccat gctttcgagc ctcagcgtca gttggggacc      180
```

-continued

```
cagctactat cctgttcgct acccatgctt tcgagcctca gcgtcagtta cagaccagac    240
agccgccttc gccactggtg ttcttccata tatctacgca tttcaccgca cagaccagac    300
agccgccttc gccactggtg ttcttccata tatctacgca tttcaccgca cagaccagac    360
agccgccttc gccactggtg ttcttccata tatctacgca tttcaccgca cagaccagac    420
agccgccttc gccactggtg ttcttccata tatctacgca tttcaccgct acacatggag    480
ttccactgtc ctcttctgca ctcaagtctc ccagtttcca atgcacttct acacatggag    540
ttccactgtc ctcttctgca ctcaagtctc ccagtttcca atgcacttct acacatggag    600
ttccactgtc ctcttctgca ctcaagtctc ccagtttcca atgcacttct acacatggag    660
ttccactgtc ctcttctgca ctcaagtctc ccagtttcca atgcacttct tcggttgagc    720
cgaaggcttt cacattagac ttaaaagacc gcctgcgctc gctttacgct tcggttgagc    780
cgaaggcttt cacattagac ttaaaagacc gcctgcgctc gctttacgct tcggttgagc    840
cgaaggcttt cacattagac ttaaaagacc gcctgcgctc gctttacgct tcggttgagc    900
cgaaggcttt cacattagac ttaaaagacc gcctgcgctc gctttacgcc caataaatcc    960
ggataacgct tgccacctac gtattaccgc ggctgctggc acgtagttac caataaatcc   1020
ggataacgct tgccacctac gtattaccgc ggctgctggc acgtagttac caataaatcc   1080
ggataacgct tgccacctac gtattaccgc ggctgctggc acgtagttac caataaatcc   1140
ggataacgct tgccacctac gtattaccgc ggctgctggc acgtagttag ccgtggcttt   1200
ctggttaaat accgtcactg ggtgaacagt tactctcacc cacgttcttg ccgtggcttt   1260
ctggttaaat accgtcactg ggtgaacagt tactctcacc cacgttcttg ccgtggcttt   1320
ctggttaaat accgtcactg ggtgaacagt tactctcacc cacgttcttg ccgtggcttt   1380
ctggttaaat accgtcactg ggtgaacagt tactctcacc cacgttcttc tttaacaaca   1440
gagctttacg agccgaaacc cttcttcact cacgcggcgt tgctccatcc tttaacaaca   1500
gagctttacg agccgaaacc cttcttcact cacgcggcgt tgctccatcc tttaacaaca   1560
gagctttacg agccgaaacc cttcttcact cacgcggcgt tgctccatcc tttaacaaca   1620
gagctttacg agccgaaacc cttcttcact cacgcggcgt tgctccatca gacttgcgtc   1680
cattgtggaa gattccctac tgctgcctcc cgtaggagtc tgggccgaca gacttgcgtc   1740
cattgtggaa gattccctac tgctgcctcc cgtaggagtc tgggccgaca gacttgcgtc   1800
cattgtggaa gattccctac tgctgcctcc cgtaggagtc tgggccgaca gacttgcgtc   1860
cattgtggaa gattccctac tgctgcctcc cgtaggagtc tgggccgact ggccgtcgtt   1920
ttactggccg tccgttttac atggccgtcg ttttacaatg gccgtccgtt ataca         1975
```